United States Patent [19]

Abrahmsohn

[11] Patent Number: 5,192,527
[45] Date of Patent: Mar. 9, 1993

[54] METHOD OF REVERSING LOCAL ANESTHESIA AND REAGENT SYSTEM THEREFOR

[76] Inventor: Glenn M. Abrahmsohn, 5055 Collins Ave., Miami, Fla. 33140

[21] Appl. No.: 812,409

[22] Filed: Dec. 23, 1991

Related U.S. Application Data

[63] Continuation-in-part of Ser. No. 723,899, Jul. 1, 1991, abandoned.

[51] Int. Cl.$^5$ .............. A61K 49/00; A61K 33/14; A61K 33/00; A61K 31/70
[52] U.S. Cl. ........................ 424/10; 424/678; 424/717; 514/23
[58] Field of Search ............ 424/10, 678, 722, 717; 514/23

[56] References Cited

U.S. PATENT DOCUMENTS

| | | | |
|---|---|---|---|
| 2,746,901 | 5/1956 | Bruce | 167/65 |
| 4,091,090 | 5/1978 | Sipos | 424/45 |
| 4,105,760 | 8/1978 | Szegtli | 424/180 |
| 4,476,115 | 10/1984 | Reed | 424/164 |
| 4,659,714 | 4/1987 | Watt-Smith | 514/260 |
| 4,937,078 | 6/1990 | Mezei | 424/450 |
| 4,963,345 | 10/1990 | Forrest | 424/10 |

OTHER PUBLICATIONS

"Molecular Mechanisms of Local Anesthesia: A Review", by John F. Butterworth, Gary R. Strichartz. Anesthesiology 72:711-754, 1990. Pertinent pages:7-20-721.

Primary Examiner—Frederick E. Waddell
Assistant Examiner—Raymond J. Henley, III
Attorney, Agent, or Firm—Foley & Lardner

[57] ABSTRACT

A method of controlling the duration of local anesthesia and a reagent system or kit for inducing and limiting the duration of local anesthesia is described.

15 Claims, No Drawings

METHOD OF REVERSING LOCAL ANESTHESIA AND REAGENT SYSTEM THEREFOR

CROSS-REFERENCE TO RELATED APPLICATION

This application is a continuation-in-part of U.S. Ser. No. 07/723,899 filed Jul. 1, 1991, now abandoned, which application Ser. No. 07/723,899 is hereby incorporated by reference.

BACKGROUND OF THE INVENTION

The present invention relates to anesthesia, especially local anesthetics. More particularly, this invention relates to a method for controlling the duration of local anesthesia, and to a reagent system or kit for inducing and limiting or reversing local anesthesia produced.

Anesthetic agents are pharmacologically active agents that block nerve conduction when applied in therapeutically effective amounts. They can be used for local application, namely to a localized area, for example, by application to the skin or other dermal membrane, or for systemic application, e.g., by the intraperitoneal or intravenous routes of administration.

The anesthetic agent may be applied locally by injection, ointments, jellies, topical solutions and suspensions or other forms known for topical administration.

Local anesthetics generally are esters or amides of benzoic acid, typically administered as an acid addition salt in dosages known to those skilled in the art.

For example, as applied to the region of the mouth and adjacent areas of humans, anesthesia involves injection of anesthetic agents including roughly 2 to 3% lidocaine, 2 to 3% mepivacaine, 0.5% marcaine or 3 to 4% prilocaine, usually administered in aqueous solution in the form of a water-soluble acid-addition salt, typically the hydrochloride salt. Also, as practiced, vasoconstricting agents such as epinephrine, phenylphrine or levonordenphedrine may be administered concomitantly or separately with the local anesthetic agent in order to prolong the duration of the local anesthesia, reportedly by constriction of blood vessels, resulting in prolongation of the contact of the anesthetic with the nerve.

Aqueous Lidocaine hydrochloride in sodium bicarbonate has been used in spinal and epidural anesthesia to speed up the onset of anesthesia to reduce the burning upon injection and to lengthen the duration of action.

In some areas, especially in the mouth, the local anesthesia may last longer than needed. This is debilitating and restrictive to the patient's normal activity. The administration of a local anesthetic at relatively low pH, typically in the range of about pH 2 to about pH 5.5, has been reported to retard the duration of anesthetic action.

SUMMARY OF THE INVENTION

The inventor has discovered that the duration of the local anesthesia can be reversed or limited by the subsequent administration of an inorganic or organic salt reversing agent in a fluid which is preferably an aqueous solution having a pH equal to or greater than about pH 7, preferably a pH of about 7 to about 8.5. The upper limit of the pH is not critical except that, in practice, the upper limit of the pH is affected by the nature of the salt, and any buffer, the concentration of base used to adjust the pH.

This invention thus provides a method of limiting duration of local anesthesia or reversing the anesthesia. This method is comprised of the steps of (a) administering an effective amount of an anesthetic agent to a local area of the subject; and (b) subsequently administering an effective amount of a reversing agent which is an inorganic or organic salt in a fluid having a pH equal to or greater than pH 7. The reversing agent limits the duration of anesthesia activity. Optionally, the reversing agent can be in buffered solution or the anesthetic agent can be applied in conjunction with a vasoconstrictor to prolong the anesthetic action, or both.

This invention also includes a reagent system for use in the method which comprises (a) first container containing an anesthetic agent and (b) a second container containing a reversing agent which is an inorganic or organic salt in a fluid having a pH of at least about 7, and preferably about pH 7 to 8.5.

The reversing agent is preferably administered in the form of a pharmaceutically acceptable pyrogen free mixture, preferably an aqueous solution in a concentration of about 4.0% to about 8.4% by weight, though concentrations substantially greater than 8.4% and substantially less than 4.0% will also reverse the duration of the local anesthesia. The amount of reversing agent administered, as known in the art, depends on the size and body weight of the patient, the area to be anesthetized, the route of administration and the concentration of anesthetic agent, but is typically approximately 1.8 to 6.0 cubic centimeters of a mixture of the foregoing concentration.

The inorganic or organic salt of the reversing agent is preferably the salt of a weak acid, and strong base, or weak base.

The method and reagent can optionally be used in conjunction with a vasoconstrictor to prolong the duration of the action.

In a preferred embodiment of this invention, the anesthetic agent is lidocaine or mepivacaine, preferably in the form of the hydrochloride acid-addition salt, and the reversing agent is sodium bicarbonate, calcium gluconate or calcium chloride.

DETAILED DESCRIPTION OF THE INVENTION

The method of this invention relates to limiting the duration of local anesthesia or reversing anesthesia in a subject, comprising the steps of (a) administering an effective amount of an anesthetic agent to a local area of a subject to produce anesthesia; and (b) subsequently applying an effective amount of a non-toxic inorganic or organic salt reversing agent in a fluid having a pH equal to or greater than about pH 7, in order to limit the duration of anesthesia or reverse anesthesia.

The term "subject" according to the present invention is intended to include all warm-blooded mammals, preferably humans.

The term "anesthetic agent" used here refers to non-toxic and for injection, pyrogen free substance known to be suitable for inducing local anesthesia in warm-blooded mammals and includes a large class of known compounds which generally are esters or amides of benzylic acid derivatives, typically administered for convenience in the form of an aqueous solution of an acid addition salt. Anesthetics useful for this purpose include lidocaine, bupivicaine, chloroprocaine, editocaine, mepivacaine, prilocaine, procaine and tetracaine, all of which are commercially supplied for use as local anesthetics in the form of the hydrochloride acid-addition salt typically in aqueous solution. Other useful amines or amides suitable as local anesthetics include benoxinate, proparacaine, dibucaine, diclonine and pramoxine. Less suitable are local anesthetics of low solubility including benzocaine and small quantities of the toxins tetrodotoxin and saxitoxin. Also less suitable because of its addictive properties is cocaine.

The term "local anesthesia" is commonly understood by the skilled artisan to mean an anesthesia having an effect only to one spot or part and not general.

The term "effective amount" as applied to the anesthetic agent means amounts known to be effective for topical application. Such amounts depend on the agent to be used, the location of administration and the form of the anesthetic. In general, lidocaine is commercially available as the hydrochloride and is used in preparations in about 0.5 to about 20% by weight, volume, some with and some without epinephrine for infiltration, about 1 to 2% for block and about 5% for topical mucosal anesthesia. Bupivicaine is used commercially as the hydrochloride in solutions from about 0.25 to about 0.75%; chloroprocaine is used as the hydrochloride in solutions of about 1 to 3%. Ediocaine is used as the hydrochloride in solutions of about 1 to 2%. Mepivicaine is used in solutions of about from 1 to 3% with or without levonordenphedrine as a vasoconstrictor. Prilocaine is used as the hydrochloride in solution at about 4% with or without epinephrine as a vasoconstrictor. Procaine is used as the hydrochloride in solutions of about 0.25 to 0.5% for infiltration, 0.5% to 2% for peripheral nerve block and 10% for spinal anesthesia. Tetracaine is used in solutions as the hydrochloride of about 5% as an ointment and about 2% for application to the mucous membranes or throat. Tetracaine for injection is available in solutions or ampules containing the dry salt, as well as ointments of 5% and creams of 1%.

The term "non-toxic" used here means that the agent should not cause any permanent damage to the nerve structure. In addition, its systemic toxicity should be low because the anesthetic agent is eventually absorbed from the site of application. In addition, anesthetic agent is preferably not irritating to the tissue to which it is applied.

The term "pyrogen free" when applied to the agents used for injection means that the mixture in question does not contain substances known to cause a pyrogenic response. Pyrogens can be removed from any mixtures by methods known in the art.

Typically, the local anesthetic is administered in a solution from about 0.5 to 5% and in other mixtures of up to 20% or 30% or more by weight/volume. The amount administered for any local anesthesia depends on the route or locale for administration. For application to the oral cavity, the amount used generally is no more than 6 cubic centimeters ("cc") of a 2% solution. Preferably the salt is administered in a concentration of from about 2% to 10% in an amount of about 0.5 to 6 cc.

The anesthesia is applied locally in known ways including surface anesthesia, infiltration, field block anesthesia, nerve block anesthesia, intravenous regional anesthesia, spinal anesthesia and epidural anesthesia. Surface anesthesia involves topical application to the mucous membranes such as those found in the nose, mouth, throat, tracheo- bronchial tree, esophagus and the genitourinary tract. Infiltration anesthesia consists of an injection of the anesthetic directly into the tissue to be incised or mechanically stimulated. This anesthesia can be superficial so as to include only the skin or include deeper structures including intraabdominal organs when they are infiltrated. Infiltration or other regional anesthetic techniques permit good anesthesia without disruption of normal body functions. Field block anesthesia is produced by subcutaneous injection of the local anesthetic to interrupt nerve transmission proximal to the site to be anesthetized. Nerve block anesthesia involves injection of the anesthetic into or about individual or peripheral nerves or nerve plexus to produce greater areas of anesthesia than the previous methods. Intravenous regional anesthesia involves injection of the solution into a vein of an extremity previously exsanguinated and kept exsanguinated. Spinal anesthesia involves injection of the anesthetic into the lumbar subarachnoid space. Epidural anesthesia involves injection of the anesthetic into the epidural space.

After local anesthesia has been accomplished, the anesthesia can then be reversed or limited by the administration of an effective amount of a non-toxic, preferably pyrogen free inorganic or organic salt reversing agent in a fluid having a pH equal to or greater than about pH 7, preferably a pH of about 7 to about 9 and more preferably a pH of about 7 to 8.5. The upper limit of the pH of the reversing agent is not critical. However, in practice, the upper limit of pH is determined by the nature of the salt, any buffer or base present, and the concentration of the foregoing. Additionally, the sensitivity of the skin to basic substances is such that a pH of not more than 10 and preferably not more than 9 is preferred.

The term "inorganic or organic salt" when used with reference to the reversing agent refers to a non-toxic, preferably water soluble, salt in a preferably pyrogen free mixture which is capable of being adjusted to a pH of at least 7 and preferably at least about a pH of 7.0 and more preferably a pH of 8. The salt is preferably an alkali or alkaline earth metal salt of an inorganic and organic acid. In order to achieve the desired pH, the salt should either be the salt of a weak acid and strong base, or of a weak acid and a weak base.

Typical cations of the salt are sodium, potassium, calcium and magnesium. Typical anions are monovalent inorganic anions such as fluoride, bromide and chloride; multivalent organic anions such as carbonate, hydrogen carbonate; and multivalent inorganic anions such as sulfate and phosphate. Non-toxic inorganic anions of organic acids include anions of mono-like and dibasic organic acids such as the acetate, gluconate and monoordicarboxylic acids.

Preferred reversing agents are sodium bicarbonate, calcium gluconate and calcium chloride.

In order to maintain the salt at the desired pH, the salt can be administered in a buffer which will maintain the mixture containing the salt at a pH of at least 7 and preferably a pH of at least 7.8 and more preferably a pH from about 7 to 8.5. Typical buffers are those known in the art and include inorganic and organic buffers including phosphate, citrate, bicarbonate and the like.

As used herein, reference to "affecting" the duration of local anesthesia and "to reverse or limit" the duration of anesthesia means that the administration of the inorganic or organic salt serves to significantly reduce the duration of anesthesia over that which would occur in the absence of the reversing agent. This affecting of the duration of anesthesia may involve merely shortening the duration of action or totally reversing the anesthesia upon the administration. The amount of reversing agent administered determines whether the anesthesia is limited or totally reversed. The amount of reversing agent necessary is dependent on whether limitation or reversal is desired, the half life of the anesthetic agent by the route of administration used and the timing of the administration of the reversing agent. Appropriate dosages in amounts will be apparent to one skilled in the art or can be determined by simple routine experimentation.

The term "effective amount" when applied to the reversing agent refers to an amount necessary to reverse or limit the anesthesia that has been induced. As indicated, this amount can be determined by a person skilled in the art and typically is a molar amount or concentration at least equal to or less than the molar amount of the anesthetic agent that has been injected or the remaining unmetabolized anesthetic agent in the area of application.

As is known in the art, the anesthetic agent can be administered concomitantly with a vasoconstrictor to prolong the duration of action. The term "vasoconstrictor" used here means an agent capable of causing constriction of blood vessels including various sympathomimetic drugs such as epinephrine, norepinephrine, levonordenphedrine and dopamine.

Typically, epinephrine is administered in a dilution of 1:100,000 mixed with a solution of lidocaine and supplied in 1.8 cc capsules.

In accordance with the method of this invention, the reversing salt is preferably administered in a non-toxic, pyrogen free fluid mixture.

The term "fluid" used here means any vehicle suitable for topical administration including solutions in suspensions for injections, ointments, jellies, topical solutions in suspensions and other forms known for topical administration. To the extent the anesthetic agent is administered by injection, then the reversing solution to achieve its optimal effectiveness should also be administered by injection. Where injections are used, the fluid of the reversing solution is conveniently water. In any event, the reversing agent is administered by the same means and route as the anesthesia.

Most conveniently, the salt is present, depending upon the solubility of the salt, in an amount of approximately 1 molar in aqueous solution. In the case of sodium bicarbonate, a 1 molar, or meq/ml (84 mgs/ml) solution has a pH of about 7.8. Such a solution is conveniently contained in an individual dosage unit of a size of approximately 1.8 cc where application to the oral cavity is concerned.

As indicated above, the pH of the reversing mixture is equal to or greater than about 7 and more preferably about 7 to 8.5 or 9.0 Use of a reversing salt having a pH of greater than 9 tends to be less effective and thus is not as desirable as use of a reversing solution at a pH of about 7 to 8.9. The reversing mixture can be a simple mixture of a vehicle and the salt. Alternatively, the reversing solution can contain a buffer to maintain the pH at the desired level.

The amount of the solution used, particularly with respect to reversing of anesthesia in the oral cavity, is about 0.6 to 6.6 cc when the reversing agent is present in a concentration of 4.0 to 8.4% by weight.

In one embodiment of the present invention, the reversing agent is administered at a concentration of 2% to 10% by weight/volume in an amount of about 0.5 to 6 cc. In a preferred embodiment, the reversing agent is sodium bicarbonate in a solution of about 8% by weight and having a pH of about 7 to 9.

Another feature of this invention is a reagent system for use in inducing and reversing the local anesthesia. Such system conveniently includes a container such as a carpule which contains the local anesthetic agent, a container or carpule of sodium bicarbonate for reversing the anesthesia, and optionally a container or carpule containing other substances to be used in conjunction therewith, for example, calcium ion for relieving any conduction block produced by the anesthetic. Instead of carpules, the system may alternatively include other known containers suitable for delivering their contents to the site of anesthesia.

In one example, the reagent system of the invention is comprised of carpule containing a the local anesthetic and a vasoconstrictor and a carpule containing sodium bicarbonate solution for reversing the local anesthesia.

The solutions for use in this invention can contain additional additives known for use in sterile pharmaceutical solutions and suspensions including, but not limited, to stabilizers, antimicrobial agents, suspending agents and other ingredients known to enhance the use and shelf life of the products of this invention.

Further objects and advantages of this invention will be apparent from the following examples. In the following examples, all references to anesthetic agents refer to the agent administered in the form of the hydrochloride salt, "meq" refers to milliequivalent, "ml" refers to milliliters, "mgs" refers to milligrams, percentages refers to percentages by volume in the case of two or more liquids, and percent by weight to percent by volume in the case of solids and liquids, "cc" refers to cubic centimeters. The following examples are given by way of illustration and should not be considered to limit the invention.

| METHODS OF SAMPLE EXPERIMENTS TO SUPPORT THE INVENTION | | |
|---|---|---|
| Initial injection and controls = anesthetizing agents | | |
| I | lidocaine | 2% |
| II | lidocaine | 2% with 1:100,000 epinephrine |
| III | mepivacaine | 3% plain |
| IV | mepivacaine | 2% with 1:20,000 levonordenphedrine |
| Second injection = potential reversal agents | | |
| 0.5 cc | NaHCO3 8.4% sodium bicarbonate 1 meq/ml (84 mgs/ml sod. bicarb.) | |
| 0.5 cc | 0.9% NaCl — pH 5.5 (9 mg NaCl/ml) | |
| 0.5 cc | 0.9% NaCl + acid (dilute hydrochloric acid 1:500 2 mg/ml) (3 cc of 0.9% NaCl with 0.05 cc of HCl to pH 5.00) | |

Experiment Design

Subjects received injections to right or left arms at several sites. The first injection, usually 0.5 cc–0.6 cc, was followed by a second injection of the same volume to the same site as the initial injection. The second injection was placed within 5 to 20 minutes of the first injection.

Pin prick tests were done every 5 minutes until sensation returned at all sites (usually by 6 hours). Tests were conducted double blind.

EXPERIMENT I

Initial Injection - 0.5 cc of 2% lidocaine
with 1:100,000 epinephrine at all sites
Control = Solution D
Second Injection - Solutions
    A. 0.5 cc of 0.9% NaCl + acid (dilute HCl 1:500 2 mg/ml) pH 5.0
    B. 0.5 cc of 8.4% NaHCO3 (1 meq/ml sodium bicarbonate) pH 7.8
    C. 0.5 cc of 0.9% NaCl solution pH 5.5
    D. Control - 0.5 cc solution of 2% lidocaine with epinephrine

| Second Injection results | Time to positive pin prick |
|---|---|
| A. 0.9 NaCl + acid | 5 hours 50 min. |
| B. 8.4% NaHCO3 | 45 minutes |
| C. 0.9 NaCl | 5 hours 50 min. |
| D. 2% lidocaine w/epinephrine | 5 hours 50 min. |

Results: Solution B reversed the local anesthesia in 45 minutes, i.e., around 1/6 of the control time.

EXPERIMENT II

Initial Injection - 0.5 cc of 2% lidocaine with 1:100,000 epinephrine at all sites
Control = Solution C
Second Injection - Solutions
    A. 0.5 cc NaCl - 0.9 normal solution 0.5 cc pH 5.5
    B. 0.5 cc 8.4% sodium bicarbonate pH 7.8
    C. Control - 0.5 cc 2% lidocaine with 1:100,000 epinephrine pH 5.5

| Second Injection - results | Time to positive pin prick |
|---|---|
| A. NaCl | 3 hours 35 min. |
| B. NaHCO3 | 1 hour 25 min. |
| C. Control 2% lidocaine with 1:100,000 epinephrine | 3 hours 35 min. |

Results: Solution B was positive after 1 hour 25 minutes or reversal achieved in less than half the control time.

EXPERIMENT III

Initial Injection - 0.5 cc lidocaine 2% plain without vasoconstrictor at all sites
Control = Solution C
Second Injection - Solutions
    A. 0.5 cc NaCl - 0.9 normal solution pH 5.5
    B. 0.5 cc 8.4% NaHCO3 - pH 7.8
    C. 0.5 cc 2% lidocaine pH 5.0

| Second Injection - Results | Time to positive pin prick |
|---|---|
| A. NaCl | 2 hours 5 min. |
| B. NaHCO3 | 1 hour |
| C. Lidocaine | 2 hours 15 min. |

Results: Solution B was positive after 1 hour or reversal achieved in less than half the control time.

EXPERIMENT IV

Initial Injection - 0.5 cc of 2% mepivacaine with 1:20,000 levonordenphedrine at all sites pH 4.5
Control = Solution C
Second Injection - Solutions
    A. 0.5 cc NaCl - 0.9 normal solution pH 5.5
    B. 0.5 cc NaHCO3 - 8.4% - 1 meq/ml - pH 7.5
    C. 0.5 cc 2% mepivacaine + 1:20,000 levonordenphedrine pH 4.5

| Second Injection - results | Time to positive pin prick |
|---|---|
| A. NaCl | 3 hours 20 min. |
| B. NaHCO3 | 1 hour 55 min. |
| C. Mepivacaine + levonordenphedrine | 3 hours 20 min. |

Results: Solution B was positive after 1 hour and 55 minutes resulting in a reversal of about roughly one-half time than the control time.

EXPERIMENT V

Initial Injection - 0.5 cc 3% mepivacaine plain at all sites pH 4.5–5.0
Control = Solution C
Second Injection - Solutions
    A. 0.5 cc NaCl 0.9 normal solution pH 5.5
    B. 0.5 cc 8.4% NaHCO3 pH 7.8
    C. 0.5 cc 3% mepivacaine plain

| Second Injection - results | Time to positive pin prick |
|---|---|
| A. NaCl | 2 hours 10 min. |
| B. NaHCO3 | 1 hour 20 min. |
| C. Mepivacaine | 2 hours 40 min. |

Results: Solution B was positive after 1 hour 20 minutes or resulting in a reversal in half the time of the control.

EXPERIMENT VI

Initial Injection - 0.6 cc of 2% lidocaine with 1:100,000 epinephrine at all sites
Control = Solution E
Second Injection - Solutions
    A. 0.6 cc Bacteriostatic H2O pH 5.5
    B. 0.6 cc 4.0% NaHCO3 pH 7.5
    C. 0.6 cc 8.4% NaHCO3 pH 7.8
    D. 0.6 cc NaCl - 0.9 normal pH 5.0
    E. 0.6 cc 2% lidocaine with 1:100,000 epinephrine pH 4.5

| Second Injection - results | Time to positive pin prick |
|---|---|
| A. H2O | 6 hours 59 min. |
| B. 4.0% NaHCO3 | 5 hours 46 min. |
| C. 8.4% NaHCO3 | 5 hours 10 min. |
| D. 0.9 N aqueous NaCl | 4 hours 9 min. |
| E. 2% lidocaine with 1:100,000 epinephrine | 8 hours 53 min. |

Results: Solution C achieved a faster reversal than Solution B. Both Solution C and Solution B achieved reversal in less time than the control (Solution E)

EXPERIMENT VII

Initial Injection - 0.6 cc of 2% carbocaine with 1:100,000 levonordenphedrine at all sites pH 4.5
Control = Solution E
Second Injection - Solutions
    A. 0.6 cc 4.0% NaHCO3 pH 7.5
    B. 0.6 cc 8.4% NaHCO3 pH 7.8
    C. 0.6 cc NaCl - 0.9 normal pH 5.0
    D. 0.6 cc Bacteriostatic H2O pH 5.5
    E. 0.6 cc 2% carbocaine with 1:100,000 levonordenphedrine 1:100,000 epinephrine levonordenphedrine pH 4.5

| Second Injection - results | Time to positive pin prick |
|---|---|
| A. 4.0% NaHCO3 | 3 hours 46 min. |
| B. 8.4% NaHCO3 | 1 hour 43 min. |
| C. NaCl | 6 hours 53 min. |
| D. H2O | 8 hours 13 min. |
| E. 2% lidocaine with 1:100,000 levonordenphedrine | 8 hours 10 min. |

Results: Solution B achieved a faster reversal than solution A. Both Solution B and Solution A achieved reversal in about one third to one half less time than the control (Solution E).

EXPERIMENT VIII

Initial Injection - 0.6 cc of 3.0% carbocaine plain without vasoconstrictor at all sites pH 4.5–5.0
Control - Solution E
Second Injection - Solutions
    A. 0.6 cc H2O pH 5.5
    B. 0.6 cc 4.0% NaHCO3 pH 7.5
    C. 0.6 cc 8.4% NaHCO3 pH 7.8
    D. 0.6 cc NaCl - 0.9 normal pH 5.0
    E. 0.6 cc 3.0% carbocaine

| Second Injection - results | Time to positive pin prick |
|---|---|
| A. H2O | 1 hour 7 min. |

EXPERIMENT VIII-continued

| | | |
|---|---|---|
| B. 4.0% NaHCO3 | | 33 min. |
| C. 8.4% NaHCO3 | | 32 min. |
| D. NaCl | 1 hour | 30 min. |
| E. 0.6 cc 3.0% carbocaine | 1 hour | 33 min. |

Results: Solution C achieved a slightly faster reversal than Solution B. Both Solution C and Solution B achieved reversal in less time than the control (Solution E).

EXPERIMENT IX

Initial Injection - 0.5 cc of 2% lidocaine with 1:100,000 epinephrine at all sites.
Control - Solution E
Second Injection - Solutions
 A. 0.5 cc H2O pH 5.5
 B. 0.5 cc water adjusted to pH 11.5 with 0.1 N sodium hydroxide
 C. 0.5 cc 8.4% aqueous NaHCO3 pH 7.8
 D. 0.5 cc H2O adjusted to pH 12 with 0.1 N sodium hydroxide
 E. 0.5 cc 2% lidocaine with 1:100,000 epinephrine pH 5.0

| Second Injection - results | Time to positive pin prick |
|---|---|
| A. H2O | 5 hours 13 minutes |
| B. H2O adjusted to pH 11.5 with 0.1 N sodium hydroxide | 7 hours 22 minutes |
| C. 8.4% NaHCO3 | 4 hours 36 minutes |
| D. Sterile H2O adjusted to pH 12 with 0.1 N sodium hydroxide | >7 hours 55 minutes |
| E. 2% lidocaine with 1:100,000 epinephrine | 5 hours 14 minutes |

Results: Solution C achieved the fastest reversal. Solutions B and D achieved a reversal in greater time than the control solution (E).

EXPERIMENT X

Initial Injection - 0.5 cc of 2% carbocaine plain without vasoconstrictor at all sites pH 4.5-5.0.
Control - Solution E
Second Injection - Solutions
 A. 0.5 cc H2O pH 5.5
 B. 0.5 cc water pH adjusted to 11.5 with 0.1 N sodium hydroxide
 C. 0.5 cc water adjusted to pH 12 with 0.1 N sodium hydroxide
 D. 0.5 cc 8.4% NaHCO3 pH 7.8
 E. 0.5 cc 2% carbocaine plain without vasoconstrictor at all sites pH 4.5-5.0

| Second Injection - results | Time to positive pin prick |
|---|---|
| A. H2O | 21 minutes |
| B. 0.5 cc water adjusted to pH 11.5 with 0.1 N sodium hydroxide | 21 minutes |
| C. 0.5 cc water adjusted to ph 12 with 0.1 N sodium hydroxide | 10 minutes |
| D. 8.4% aqueous NaHCO3 | 20 minutes |
| E. 2% carbocaine | 1 hour 24 minutes |

Results: Solution C achieved the fastest reversal. Solutions A, B, and D achieved a faster reversal than the control solution E.

EXPERIMENT XI

Initial Injection - 2% carbocaine with 1:100,000 levonordenphedrine at all sites.
Control - Solution E
Second Injection - Solutions
 A. 0.5 cc H2O pH 5.5
 B. 0.5 cc water adjusted to pH 11.5 with 0.1 N sodium hydroxide
 C. 0.5 cc water adjusted to pH 12 with 0.1 N sodium hydroxide
 D. 0.5 cc 8.4% NaHCO3 ph 7.8
 E. 0.5 cc 2% carbocaine with 1:100,000 levonordenphedrine pH 4.5

| Second Injection - results | Time to positive pin prick |
|---|---|
| A. H2O | 6 hours |
| B. 0.5 cc water adjusted to pH 11.5 with 0.1 N sodium hydroxide | 7 hours 49 minutes |
| C. 0.5 cc water adjusted to pH 12 with 0.1 N sodium hydroxide | 7 hours 49 minutes |
| D. 8.4% NaHCO3 | 49 minutes |

EXPERIMENT XI-continued

| | |
|---|---|
| E. 2% carbocaine with 1:100,000 levonordenphedrine | 7 hour 51 minutes |

Results: Solution D achieved the fastest reversal. Solution A achieved a faster reversal than control solution E.

CONCLUSION

The above experiments confirm the hypothesis of the invention. The tests have shown that 4.0% and 8.4% NaHCO3 solutions can reduce or reverse the local anesthetic working times. Furthermore, 8.4% NaHCO3 solutions achieve a faster reversal of the local anesthetic than 4.0% NaHCO3 solutions.

What is claimed:

1. A reagent system for inducing and limiting the duration of local anesthesia comprising:
 (a) a first container containing an anesthetic agent; and
 (b) a second container containing an inorganic or organic salt reversing agent which when diluted with a fluid has a pH of at least about 7.

2. The reagent system of claim 1, wherein the anesthetic agent and the reversing agent are individually present in a pharmaceutically acceptable, non-toxic pyrogen free solution.

3. The reagent system of claim 2, wherein the solution of the local anesthetic agent also contains a vasoconstrictor.

4. The reagent system of claim 1, wherein the inorganic or organic salt reversing agent is selected from the group consisting of sodium bicarbonate, calcium gluconate and calcium chloride.

5. The reagent system of claim 2, wherein the inorganic or organic salt reversing agent is in an aqueous buffered solution.

6. A method of limiting the duration or reversing the action of a local anesthetic in a subject comprising the steps of:
 (a) administering an effective amount of an anesthetic agent to a local area of the subject to produce anesthesia; and
 (b) subsequently administering an effective amount of a non-toxic, inorganic or organic salt reversing agent in a fluid having a pH equal to or greater than about pH 7, wherein the reversing agent limits the duration of the anesthesia.

7. The method of claim 6, wherein the fluid contains a buffer.

8. The method of claim 7, further comprising the administration of an effective amount of a vasoconstrictor at or about the time and location of administration of the anesthetic agent.

9. The method of claim 6, wherein the reversing agent is an inorganic or organic salt derived from a weak acid.

10. The method of claim 9, wherein the reversing agent is selected from the group consisting of sodium bicarbonate and calcium gluconate.

11. The method of claim 6, wherein the reversing agent is a calcium salt.

12. The method of claim 11, wherein the calcium salt is calcium chloride.

13. The method of claim 6, wherein the reversing agent is administered at a concentration of about 2% to about 10% by weight/volume in an amount of about 0.5 to 6 cc.

14. The method of claim 13, wherein the reversing agent is sodium bicarbonate.

15. The method of claim 14, wherein the sodium bicarbonate is in a solution of about .8% by weight and having a pH of about 7 to about 9.

* * * * *